United States Patent
Childress et al.

(10) Patent No.: US 6,809,213 B2
(45) Date of Patent: Oct. 26, 2004

(54) PREPARATION OF SECONDARY AMINOISOBUTYLALKOXYSILANES

(75) Inventors: R. Shawn Childress, Marietta, OH (US); Michelle A. Filipkowski, Marietta, OH (US); Curtis L. Schilling, Jr., Marietta, OH (US)

(73) Assignee: General Electric Company, Pittsfield, MA (US)

( * ) Notice: Subject to any disclaimer, the term of this patent is extended or adjusted under 35 U.S.C. 154(b) by 111 days.

(21) Appl. No.: 09/847,004

(22) Filed: May 1, 2001

(65) Prior Publication Data

US 2001/0044551 A1 Nov. 22, 2001

Related U.S. Application Data

(60) Provisional application No. 60/203,098, filed on May 5, 2000.

(51) Int. Cl.$^7$ .................................................. C07F 7/10
(52) U.S. Cl. ...................... 556/413; 556/478; 556/479; 556/481
(58) Field of Search ................................ 556/413, 416, 556/417, 478, 479, 481

(56) References Cited

U.S. PATENT DOCUMENTS

| | | |
|---|---|---|
| 2,930,809 A | 3/1960 | Kenmore et al. |
| 2,970,150 A | 1/1961 | Bailey |
| 4,410,669 A | 10/1983 | Panster et al. |
| 4,455,415 A | 6/1984 | Panster et al. |
| 4,481,364 A | 11/1984 | Chu et al. |
| 4,556,722 A | 12/1985 | Quirk et al. |
| 4,645,844 A | 2/1987 | Berger et al. |
| 4,888,436 A | 12/1989 | Shiozawa et al. |
| 4,897,501 A | 1/1990 | Takatsuna et al. |
| 4,921,988 A | 5/1990 | Takatsuna et al. |
| 4,927,949 A * | 5/1990 | Kabeta et al. ............... 556/413 |
| 4,927,953 A | 5/1990 | Takatsuna et al. |
| 5,486,634 A | 1/1996 | Hahn et al. |
| 5,840,951 A | 11/1998 | Hierstetter et al. |
| 6,015,920 A | 1/2000 | Schilling et al. |
| 6,197,912 B1 | 3/2001 | Huang et al. |

FOREIGN PATENT DOCUMENTS

| | | |
|---|---|---|
| EP | 0135813 | 4/1985 |
| EP | 0676403 | 10/1995 |
| GB | 949044 | 2/1964 |
| WO | WO 01/49655 | 7/2001 |

OTHER PUBLICATIONS

Speier et al. "*Synthesis of (3–Aminoalkyl)silicon Compounds*" Journal of Org,Chem., vol. 36, No. 21, at pp. 3120–3126. (1971).

Saam et al. "*Preparation of 3–Triethoxysilylpropylamine and 1,3–Bis(3–aminopropyl)tetramethyl–disiloxane*" appearing in Journal of Organic Chemistry, vol. 24, 119 (1959).

Belyakova et al., "*Addition of Hydride Alkoxysilanes to Allyamine and its Derivatives*" Appearing in English Journal of General Chemistry—Translated from Zhurnal Obshchei Khimii, vol. 44, No. 7, pp. 1484–1489 (Jul. 1974).

\* cited by examiner

*Primary Examiner*—Jeffrey B. Robertson

(57) ABSTRACT

A highly efficient method is provided for preparing secondary aminoisobutylalkoxysilanes by reacting hydridoalkoxysilanes with secondary methallylamines in the presence of a hydrosilation catalyst.

5 Claims, No Drawings

PREPARATION OF SECONDARY AMINOISOBUTYLALKOXYSILANES

CROSS REFERENCE TO RELATED APPLICATION

This application claims priority from U.S. Provisional Application Ser. No. 60/203,098, filed May 5, 2000.

FIELD OF THE INVENTION

The present invention relates to a highly efficient method of preparing secondary aminoisobutylalkoxysilanes via noble metal-catalyzed hydrosilation reactions between secondary methallylamines and hydridoalkoxysilanes.

BACKGROUND OF THE INVENTION

Secondary aminoisobutylalkoxysilanes have long been accessible by various chemical approaches, and have recently demonstrated commercially useful performance in polyurethane sealants by providing crosslinking sites for alkoxysilane-functional polyurethanes (see EP 676,403 and U.S. Pat. No. 6,197,912, incorporated herein by reference). The preparation of such silanes has been achieved with some degree of complexity, however.

The preparation of $Me(MeO)_2SiCH_2CHMeCH_2NHMe$ is reported (Journal of Organic Chemistry, vol. 36, 3120 (1971)) via a series of reactions including the hydrosilation of methallyl chloride with $MeSiHCl_2$, reaction of that product with a large excess of $MeNH_2$, and reaction of the cyclic silazane so formed with MeOH. A similar trialkoxysilane version was made by a slightly different sequence of reactions as disclosed in Brit. 994,044, whereby methallyl chloride is hydrosilated with trichlorosilane, followed by reaction of that product with ethanol to form $(EtO)_3SiCH_2CHMeCH_2Cl$, and reaction of that product with excess $MeNH_2$ to form $(EtO)_3SiCH_2CHMeCH_2NHMe$. These two processes both involve three steps, namely hydrosilation, esterification, and amination, plus a final purification, as by distillation, such that these processes are not commercially or economically attractive. While bis (alkoxysilylisobutyl)amines, the putative products of hydrosilations of dimethallylamine with hydridoalkoxysilanes or hydridoalkylalkoxysilanes, would be very difficult to prepare by the former process involving cyclic silazane intermediates, they are reported as low yield by-products of the latter process, involving reactions of chloroisobutylalkoxysilanes with ammonia. A similar molecule is also reported as a by-product from the reduction of 2-cyanopropyltriethoxysilane (U.S. Pat. No. 2,930,809), and as a crosslinked aminosiloxane resin raw material, prepared by reaction of chloroisobutyltriethoxysilane with ammonia (U.S. Pat. Nos. 4,410,669 and 4,455,415). The product of EP 676,403, namely $Me(MeO)_2SiCH_2CHMeCH_2NHC_6H_5$, was prepared by reaction of excess aniline with $Me(MeO)_2SiCH_2CHMeCH_2Cl$ and involves the aforementioned three steps plus distillation.

There is thus a continuing need in the adhesives and sealants art for secondary aminoisobutylalkoxysilanes, including secondary bis(alkoxysilylisobutyl)amines which can be prepared in high yields and high purities by processes which are efficient in terms of both reaction time and output per unit volume of equipment used, which generate minimal amounts of waste and by-products, and which are simple in terms of number of process steps and number of raw materials, additives, or promoters which need to be charged to said equipment.

Methallylamine is disclosed and/or claimed in a number of patents involving hydrosilation of allylic amines using hydridosiloxanes, but there is no working example of such a reaction, and there has been no suggestion to hydrosilate methallylamine using a hydridosilane. In particular, there is a disclosure of hydrosilation of a secondary methallylamine with a hydridosiloxane (U.S. Pat. No. 5,486,634) and limited art on hydrosilations of tertiary methallylamines, which would yield products of no use in capping polyurethanes. There is also no working example of hydrosilation of dimethallylamine, although that amine is disclosed in at least one hydrosilation patent also involving hydridosiloxanes (U.S. Pat. No. 5,840,951).

Historically, hydrosilations of allylic amines have been notoriously unsuccessful. Allylamine is specifically excluded in an early general patent on hydrosilation (U.S. Pat. No. 2,970,150), with hydrosilation products being prepared by capping the allylamine with trimethylsilyl groups, hydrosilating the allyl group, and removing the trimethylsilyl groups (see Journal of Organic Chemistry, Vol. 24, 119 (1959)). Alternatively, aminopropylalkoxysilanes have been prepared by reactions of chloropropylalkoxysilanes with large excesses of ammonia or primary amines, yielding the respective primary or secondary aminopropylalkoxysilanes. These routes suffer from low yields per unit volume of equipment used, high levels of waste or excess raw materials, and the formation of large amounts of difficult-to-handle solid hydrochloride salts. Aminopropylalkoxysilanes have also been prepared by reduction of cyanoethylalkoxysilanes, which are prepared by hydrosilation of acrylonitrile with chlorosilanes, followed by esterification with the appropriate alcohol. These are multi-step processes, followed by purification as by distillation.

A number of later developments have allowed the noble metal-catalyzed hydrosilations of allylamine with various SiH-containing reactants, although the reactions have been impractically slow and/or incomplete, unless run at a higher temperature, usually under pressure, in the presence of a hydrosilation promoter (U.S. Pat. No. 4,481,364). Further improvements in yields have been obtained with rhodium catalysts instead of platinum catalysts, with additives or promoters being necessary both for said improved yields and for providing products with lowered contents of undesired internal isomer adducts (U.S. Pat. Nos. 4,556,722; 4,888,436; 4,897,501; 4,921,988; 4,927,953).

The situation regarding diallylamine is further complicated by the formation of disproportionation by-products, which do not occur with allylamine itself (Zhur. Obshch. Khim., Vol. 44, 1484 (1974), in English as Journal of General Chemistry, USSR, Vol. 44, 1456(1974)).

Given this history there has heretofore been no reason to expect that secondary aminoisobutylalkoxysilanes could be prepared in high yield by a direct hydrosilation reaction of an alkoxyhydridosilane and a methallylamine compound.

SUMMARY OF THE INVENTION

The present invention provides a simple, highly efficient method for preparing secondary aminoisobutylalkoxysilanes by the noble metal-catalyzed hydrosilation of secondary methallylamines with hydridoalkoxysilanes or hydridoalkylalkoxysilanes. The reactions proceed in high yields and conversions to yield isomerically pure products in the absence of additives or promoters normally required for hydrosilations of allylic amines. The process involves neither modification of the secondary methallylamines nor use of added hydrosilation promoters or solvents. Ordinary noble metal catalysts can be used.

DETAILED DESCRIPTION OF THE INVENTION

The process of the present invention is represented by the general equation:

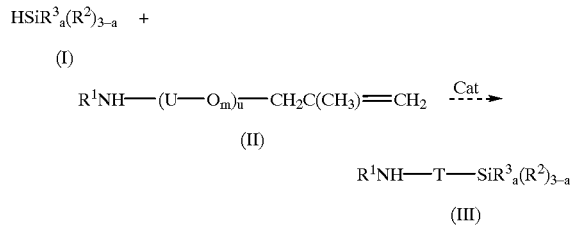

which depicts reactions between hydridoalkoxysilanes or hydridoalkylalkoxysilanes of Formula I with secondary methallyl amines of Formula II in the presence of a noble metal catalyst to yield secondary aminoisobutylalkoxysilanes of Formula III, essentially in the absence of any additive or promoter for the hydrosilation reactions. In the general equation above, $R^1$ represents an alkyl group having 1 to 30 carbon atoms, optionally interrupted with one or more ether oxygen atoms and/or substituted with a carbonyl oxygen atom, an aryl, alkaryl, or aralkyl group having 6 to 10 carbon atoms, or a group of the formula

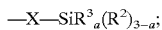

$R^2$ represents an alkoxy group having 1 to 6 carbon atoms or an aryloxy, alkaryloxy, or aralkyloxy group having 6 to 10 carbons, $R^3$ represents an alkyl group of 1 to 6 carbon atoms or an aryl, alkaryl, or aralkyl group having 6 to 10 carbon atoms; a is 0, 1 or 2; U represents a divalent linear, cyclic or branched hydrocarbon group of 1–6 carbon atoms which may be optionally interrupted by one or more ether oxygen atoms and/or substituted with a carbonyl oxygen atom; m is 0 or 1; u is 0 or 1; T is

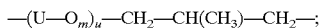

X is an alkylene group of 3 to 11 carbon atoms or T; and Cat represents an effective amount of a noble metal-containing hydrosilation catalyst.

Examples of compounds of formula I include $(MeO)_3SiH$, $Me(MeO)_2SiH$, $Me_2(MeO)SiH$, $(EtO)_3SiH$, $Me(EtO)_2SiH$, $Me_2(EtO)SiH$, or $(PrO)_3SiH$, $Me(PrO)_2SiH$, and $Me_2(PrO)SiH$ where Me is methyl, Et is ethyl, and Pr is n-propyl or 1-propyl; the corresponding butoxy, pentoxy, or hexoxy silanes; phenoxy silanes such as $Me(C_6H_5O)_2SiH$, $C_6H_5(MeO)_2SiH$; and the like. The methoxy and ethoxy silanes are preferred, particularly the trialkoxysilanes as prepared by the direct reactions of silicon metal with the corresponding alcohol. The methyldialkoxysilanes, normally prepared by esterification of the respective hydridodichlorosilane with the corresponding alcohol, are also preferred.

In general, compounds of Formula II will comprise at least a methallyl group and a secondary amine group, and may contain other hydrocarbon and oxygen functionalities, with the proviso that said functionalities do not interfere with the hydrosilation reactions. Examples of compounds of Formula II include $CH_2$=$CMeCH_2NHMe$, $CH_2$=$CMeCH_2NHEt$, $CH_2$=$CMeCH_2NHPr$, $CH_2$=$CMeCH_2NHBu$ where Et is ethyl and Pr and Bu are linear or branched propyl and butyl, $CH_2$=$CMeCH_2NHC_6H_5$, $CH_2$=$CMeCH_2NHCH_2C_6H_5$, $CH_2$=$CMeCH_2NHCH_2CH_2OR^3$, $CH_2$=$CMeCH_2NHCH_2CHMeOR^3$, $CH_2$=$CMeCH_2NH(CH_2CH_2O)_b(CH_2CHMeO)_cR^3$, where $R^3$ is as defined above and b and c are integers of 0 to 10, and b+c are at least 2, $CH_2$=$CMeCH_2NHCHCO_2R^3(CH_2CO_2R^3)$ where $R^3$ is as defined above, $(CH_2$=$CMeCH_2)_2NH$, $(CH_2$=$CMeCH_2OCH_2CH_2)_2NH$, and the like. One preferred compound of Formula II is N-ethylmethallylamine; another is N-phenylmethallylamine, and a third is dimethallylamine.

The hydrosilation catalyst is suitably a noble-metal containing hydrosilation catalyst. Suitable noble metals include platinum, rhodium, ruthenium, iridium, and osmium, with platinum being preferred. The noble metal-containing hydrosilation catalyst of the present invention may be employed in any catalytically effective form, including in compounds or solutions thereof, and as deposits on various organic or inorganic supports. Preferred catalysts are compounds of platinum, including chloroplatinic acid and solutions thereof, and the divinyltetramethyl-disiloxane platinum complex and solutions thereof. The catalyst level is an amount effective to catalyze the reaction and will typically range from about 5 to about 500 parts per million of noble metal relative to the combined weights of the reactants of Formulae I and II, with 10 to 100 parts per million being preferred.

Reaction conditions are not narrowly critical regarding temperature, pressure, ratios of reactants, or order of combination of reactants. The reaction temperature is typically elevated, in the range of 50 to 150° C., with 60 to 120° C. being preferred. For simplicity, the reactions will typically be run at atmospheric pressure. However, pressure-capable equipment and elevated pressures may be employed if desired. The reactant ratio, i.e., the molar ratio of the reactant of Formula I to that of Formula II may range from 0.2:1 to 5:1, but is generally close to 1:1 for secondary methallylamines with one methallyl group, and close to 2:1 for dimethallylamines. A slight excess of the reactant of Formula I, for example a ratio of 1.2:1 for monomethallylamines or 2.4:1 for dimethallylamines, is preferred for economic reasons.

While either reactant may be added to the other in the presence of an effective amount of hydrosilation catalyst, for certain secondary methallylamines, particularly dimethallylamine, it is preferred to add the compound of Formula II to that of Formula I at an elevated temperature. These hydrosilation reactions may also be run in continuous fashion in equipment designed for that purpose (See, for example, U.S. Pat. No. 6,015,920). Reaction times are relatively short for these reactions, which are exothermic. The latter point implies that catalysis of a total mixture of compounds of Formulae I and II is less desirable from a safety point of view.

It is an unexpected feature of the present invention that there is no need for additives or promoters beyond the hydrosilation catalyst. There is no problem of internal adduct isomer formation, and no problem of dehydrocondensation reactions between hydridosilyl groups and secondary amine groups leading to Si—N bond formation and hydrogen generation. This is particularly surprising in view of the poor reactivity of primary methallylamine, $CH_2$=$CMeCH_2NH_2$, under the same reaction conditions. The efficient reactivity of secondary methallylamines extends to dimethallylamine, which shows none of the serious issues of by-product formation, namely internal adduct and disproportionation product formation, ascribed to diallylamine. Thus, while the various additives and promoters and high reaction temperatures and pressures which have been used for allylamine may be used with secondary methallylamines, there is no requirement to do so, nor is it necessary to modify the secondary methallylamines as with trimethylsilyl groups to allow hydrosilation thereof. Thus, while many process patents dealing with hydrosilation of allylamine require the use of additives, promoters, high temperatures, or high pressures, and have disclosures or claims which include methallylamines, it has surprisingly been found that secondary methallylamines are efficiently hydrosilated with hydridoalkoxysilanes or hydridoalkylalkoxysilanes without practicing any of said processes.

There is one side reaction which is perhaps more prevalent in making secondary aminoisobutylalkoxysilanes than in making primary or secondary aminopropylalkoxysilanes. That side reaction, which ultimately yields the same desired product as the hydrosilation reaction, is the formation of cyclic silazanes by reaction of the secondary amine group with the alkoxysilane group. In general terms, the product of Formula III cyclizes to a cyclic silazane of Formula IV with generation of a molar equivalent of alcohol, $R^2H$, where $R^2$ is as defined above. This reaction is depicted below:

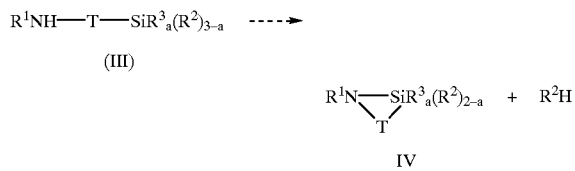

The formation of cyclic silazane is an equilibrium reaction, driven to the right by the removal of alcohol, $R^2H$. The simple addition of the appropriate equivalent of alcohol, $R^2H$, to product containing the cyclic silazane IV will regenerate the desired product III. Removal of cyclic silazane impurities is a necessary part of ensuring product purity for stoichiometric calculations used in preparing silylated polyurethanes.

It should also be noted that the products of the present invention, after stripping to remove excess reactants and excess alcohol, if used to remove cyclic silazane impurities, are of sufficient purity to be used without further purification (e.g. by distillation) in many applications. This derives from the fact that there is no mechanism to generate higher boiling bis-silyl by-products as occurs in both reactions of chloroisobutylalkoxysilanes with ammonia and of reductions of 2-cyanopropylalkoxysilanes with hydrogen. Distillation may be desireable in some cases, however, to provide incremental increase in purity and/or to remove color and catalyst residues.

It appears that a methyl/alkoxy group exchange reaction, recently observed for other hydrosilations of methyldialkoxysilanes (see U.S. Pat. No. 6,166,238, Filipkowski et al, incorporated herein by reference), does not occur to a significant extent during hydrosilations of secondary methallylamines.

The following specific examples illustrate certain aspects of the present invention and, more particularly, point out various aspects of the method for evaluating same. However, the examples are set forth for illustrative purposes only and are not to be construed as limitations on the present invention.

EXAMPLES

The abbreviations g, ml, L, mm, mol, mmol, ppm, $\mu$l, hr, kg, kmol, GC, and MS respectively represent gram, milliliter, liter, millimeter, molar equivalent, millimolar equivalent, parts per million, microliter, hour, kilogram, kilomolar equivalent, gas chromatography, and mass spectrometry. All temperatures are reported in degrees Centigrade, and all reactions were run in standard laboratory glassware or pilot scale or production units at atmospheric pressure under an inert atmosphere of nitrogen, and all parts and percentages are by weight.

Example 1

Hydrosilation of N-Ethylmethallylamine with Trimethoxysilane

A one-liter three-neck round bottom flask was equipped with a magnetic stir bar, standard heating mantle, thermocouple, addition funnel, condenser and $N_2$ inlet/bubbler. The flask was charged with 220 g (1.80 mols) of trimethoxysilane and heated to 60° C. at which temperature 0.25 ml of platinum tris(divinyltetramethyl disiloxane) diplatinum (0) (5% Pt content in toluene—referred to as Pt catalyst throughout these examples) was added. The solution was further heated to 68° C. and dropwise addition of 150 g (1.52 mols) of N-ethylmethallylamine was then conducted over a period of 45 minutes. After addition, the contents were heated to 90° C. and maintained at this temperature for 1 hr. The temperature was then increased to 105° C. and held for 4.5 hrs. Upon completion of the reaction, the mixture was cooled to room temperature and 16 g (0.5 mols) of methanol were added and gently heated prior to distillation. Final purification via vacuum distillation yielded 273 g (1.24 mols) of N-ethyl-3-trimethoxysilyl-2-methylpropanamine. The product (b.p. 98–100° C. at 12 mm Hg) was characterized via GC/MS. The isolated yield was 82%. Product structure was supported by GC/MS analysis.

Example 2

Hydrosilation of N-Ethylmethallylamine with Methyldiethoxysilane

With the exception of a distillation head replacing the condenser, the equipment was similar to that of Example 1. The flask was charged with 381 g (2.84 mols) of methyldiethoxysilane and 0.65 ml of platinum catalyst. The contents were heated to 90° C. and 260 g (2.63 mols) of N-ethylmethallylamine were added over 30 minutes via addition funnel. Immediately after addition was completed, the contents were heated to 110° C. and held for one hr. The product was isolated by vacuum distillation to give 485 g (2.08 mols) of N-ethyl-(3-diethoxymethylsilyl)-2-methylpropanamine. The product (b.p. 88–90° C. at 27 mm Hg) was characterized via GC/MS. The isolated yield was 79%.

Example 3

Hydrosilation of N-Ethylmethallylamine with Trimethoxysilane

To a 50 L jacketed glass reactor equipped with an overhead column were added 16.8 kg (167 mols) of N-ethylmethallylamine and 42 ml of platinum catalyst. The contents were then heated to 93° C. and 24.9 kg (204 mols) of trimethoxysilane were slowly added over 4 hrs. After addition was completed, the reaction mixture was heated to 105° C. and held for 2 hrs. After the cook period, the contents were cooled to below 50° C. and 1.5 L of methanol were added. The crude material was distilled to give 28.9 kg (131 mols) of material with a purity of 99%. The isolated yield of N-ethyl-3-trimethoxysilyl-2-methylpropanamine was 78% based on N-ethylmethallylamine.

Example 4

Hydrosilation of N-Ethylmethallylamine with Trimethoxysilane

To a 500 gallon reactor were added 489 kg (4.94 kmols) of N-ethylmethallylamine and 1425 g of platinum catalyst. The resulting solution was heated to 88° C. and 725 kg (5.94 kmols) of trimethoxysilane were added at such a rate to keep the temperature under 105° C. After addition was complete, the contents were heated to 110° C. for one hr. The low boiling byproducts were then removed by overhead stripping. The mixture was then cooled and approximately 60 L of methanol were added, and the reaction mixture was agitated at 50° C. for 1 hour before stripping the excess methanol. The resulting crude material (>97% purity) was then transferred from the reactor. The process was repeated without cleanup of the reactor to yield a combined total of 1638 kg (7.41 kmol) of N-ethyl-3-trimethoxysilyl-2-methylpropanamine.

Example 5

Hydrosilation of Dimethallylamine with Trimethoxysilane

To a four-neck flask equipped with a reflux condenser, addition funnel, heating mantle, thermocouple, and a magnetic stirrer were added 12.0 g (0.10 mols) of trimethoxysilane and 17 µl of platinum catalyst. This mixture was heated to 85° C. and 5.0 g (0.04 mols) of dimethallylamine were added dropwise. After completion of the addition, the reaction mixture was heated to 110° C. for 3.5 hours. The resulting mixture was analyzed by gas chromatography and GC/MS. Gas chromatography revealed that the diadduct had been formed in a yield of 81% based on the dimethallylamine.

Example 6

Hydrosilation of Dimethallylamine with Methyldiethoxysilane

The reaction was carried out similar to Example 5 except that 13.5 g (0.10 mols) of methyldiethoxysilane and 18.5 µl of platinum catalyst were charged to the flask. This solution was heated to 90° C. and 5.0 g (0.04 mols) of dimethallylamine were added dropwise. After completion of the addition, the reaction was heated to 105° C. and held for 6 hrs. The resulting mixture was analyzed by gas chromatography and GC/MS. Gas chromatography indicated that the yield of the diadduct was 97% based on the dimethallylamine.

Example 7

Hydrosilation of N-Ethylmethallylamine with Triethoxysilane

The reaction was carried out similar to Example 5 except that 5.0 g (0.03 mols) of triethoxysilane and 5 µl of platinum catalyst were charged to the flask. This solution was heated to 100° C. and 3.0 g (0.03 mols) of N-ethylmethallylamine were added dropwise. After completion of the addition, the reaction was heated to 130° C. for 3 hrs. The resulting mixture was analyzed by gas chromatography and GC/MS. Gas chromatography indicated that the yield of the N-ethyl-3-triethoxysilyl-2-methylpropanamine was 85% based on the triethoxysilane.

Example 8

Hydrosilation of Dimethallylamine with Methyldimethoxysilane

The reaction was carried out similar to Example 5 except that 15.0 g (0.12 mols) of dimethallylamine and 44 µl of platinum catalyst were charged to the flask. This solution was heated to 85° C. and 28.9 g of methyldimethoxysilane (93.8% purity, 0.26 mols) were added dropwise. After the addition was complete, the mixture was heated to 122° C. for two hrs. The reaction was then cooled and 2 ml of methanol were added. The resulting mixture was analyzed by gas chromatography and GC/MS. Gas chromatography indicated that the yield of the diadduct was 92% based on dimethallylamine.

Example 9

Hydrosilation of N-Ethylmethallylamine with Methyldimethoxysilane

The reaction was carried out similar to Example 5 except that 18 g (0.18 mols) of N-ethylmethallylamine and 40 µl of platinum catalyst were charged to the flask. This solution was heated to 85° C. and 22 g of methyldimethoxysilane (95.2% purity, 0.2 mols) were added dropwise. After the addition was complete, the mixture was heated at 110° C. for 1.5 hrs. The resulting mixture was analyzed by gas chromatography and GS/MS. Gas chromatography indicated that the yield of N-ethyl-(3-dimethoxymethyl-silyl)-2-methylpropanamine was 95% based on fN-ethylmethallylamine.

Comparative Example 1

Attempted Hydrosilation of Methallylamine with Trimethoxysilane

The reaction was carried out similar to Example 5 except that 10.5 g (0.09 mols) of trimethoxysilane and 16 µl of platinum catalyst were charged to the flask. The solution was heated to 85° C. and 5.0 g (0.07 mols) of methallylamine were added dropwise. The reaction was brought to reflux for 3.5 hours. Analysis by gas chromatography and GC/MS did not indicate any hydrosilation product.

Example 10

Hydrosilation of N-Phenylmethallylamine with Trimethoxysilane

To a 100 ml 4-neck round bottom flask, equipped with stir bar, thermocouple probe, condenser, addition funnel and nitrogen inlet/outlet, were added 12.0 ml (88.3 mmol, 1.2 equivalents) of trimethoxysilane (TMS). A solution of 5% dimethylvinylsiloxane platinum(0) catalyst in toluene (Pt(O) M*M*, 23 µl, 20 ppm Pt) was then added to the TMS in the reaction vessel. The olefin, N-phenylmethallylamine, (67.0g, 0.52 mol), which had been charged to the addition funnel, was then added drop-wise slowly to the mixture at room temperature. After olefin addition completion the sluggish reaction was then heated slowly to a maximum of 80° C. over a period of 10+ hours. An additional 30 ppm of Pt(0) catalyst was added over this period to bring the total catalyst charge to 50 ppm platinum. Final GC Analysis showed, besides TMS lites and unreacted N-phenylmethallylamine, 74.3% of desired product, N-phenyl-3-(trimethoxysilyl)-2-methylpropanamine. GC/MS Data of the above mixture support the structure of the product.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto. Further, the specific features recited in the respective dependent claims can be combined in any other manner with the features of the independent claims and any of the other dependent claims, and all such combinations are expressly contemplated to be within the scope of the invention.

Throughout the specification and claims the term "comprises" is defined as "includes," i.e. without limiting additional subject matter which may be added thereto, and the various derivatives of the term (for instance "comprising") are defined correspondingly.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

What is claimed is:

1. A method for preparing a secondary aminoisobutylalkoxysilane comprising hydrosilating a secondary methallylamine with a hydridoalkoxysilane in the presence of an effective amount of a hydrosilation catalyst, wherein the hydrosilation catalyst is a platinum metal containing catalyst, and said effective amount is from 5 to 500 parts per million by weight of platinum relative to the combined weights of the hydridoalkoxysilane and the secondary methallylamine, the molar ratio of hydridoalkoxysilane to secondary methallylamine is in the range of 0.2 to 5, and the hydrosilating step is performed at an elevated temperature in the range of 50 to 150° C., and at atmospheric pressure.

2. The method of claim 1 wherein the secondary methallylamine is a compound having a single methallyl group or dimethallylamine, the elevated temperature is in the range of 60 to 120° C. and the molar ratio of hydridoalkoxysilane to secondary methallylamine is 1 to 1.2 for secondary methallylamines with one methallyl group, and 2 to 2.4 for dimethallylamine.

3. A method for preparing a secondary aminoisobutylalkoxysilane comprising hydrosilating a secondary methallylamine with a hydridoalkoxysilane in the presence of an effective amount of a platinum hydrosilation catalyst, wherein the secondary methallylamine is added to a mixture comprising the hydridoalkoxysilane and the hydrosilation catalyst at an elevated temperature.

4. A method for preparing a secondary aminoisobutylalkoxysilane comprising hydrosilating a secondary methallylamine with a hydridoalkoxysilane in the presence of an effective amount of a platinum hydrosilation catalyst, comprising adding an alcohol to the reaction product of the hydrosilating step.

5. A method for preparing a secondary aminoisobutylalkoxysilane comprising hydrosilating a secondary methallylamine with a hydridoalkoxysilane in the presence of an effective amount of a platinum hydrosilation catalyst, comprising subsequently purifying the secondary aminoisobutylalkoxysilane.

* * * * *